United States Patent
Bak

(10) Patent No.: US 7,925,361 B2
(45) Date of Patent: Apr. 12, 2011

(54) FAULT DETECTION FOR A RESISTIVE POSITION SENSOR

(75) Inventor: Donald J. Bak, Streamwood, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 318 days.

(21) Appl. No.: 12/208,013

(22) Filed: Sep. 10, 2008

(65) Prior Publication Data

US 2010/0058830 A1    Mar. 11, 2010

(51) Int. Cl.
G05B 1/06 (2006.01)
G01R 31/02 (2006.01)

(52) U.S. Cl. ............... 700/21; 324/549; 318/663

(58) Field of Classification Search .......... 700/21, 700/55, 56, 79, 302; 702/58, 70, 80, 190–192; 324/549, 613, 772; 318/663
See application file for complete search history.

(56) References Cited

U.S. PATENT DOCUMENTS

| 4,920,939 A * | 5/1990 | Gale ............................. 123/399 |
| 6,566,837 B1 * | 5/2003 | Zhang et al. .................. 318/610 |
| 2007/0055144 A1 * | 3/2007 | Neustadter et al. ........... 600/425 |

FOREIGN PATENT DOCUMENTS

FR    2735871 A1 * 12/1996
JP    06330885 A * 11/1994

\* cited by examiner

*Primary Examiner* — Ryan A Jarrett
(74) *Attorney, Agent, or Firm* — Peter L. Kendall

(57) ABSTRACT

Circuits for detecting faults in variable resistive position feedback sensors common in the use of motion control systems, provide a filter coupled to an output signal of the variable resistive position sensor for processing the signal to detect noise indicative of intermittent faults. A memory stores occurrences of signals from the filter. The memory can activate an alarm which indicates that a failure is detected. The circuits are particularly applicable to medical imaging systems such as SPECT, PET or MRI systems which contain a multiplicity of moving components that require accurate motion control and positioning.

18 Claims, 2 Drawing Sheets

FAULT DETECTION FOR A RESISTIVE POSITION SENSOR

TECHNICAL FIELD

The present invention relates generally to a mechanism for detecting faults in resistive position feedback sensors, which are used in many different applications where motion of devices is required, and in particular in medical imaging systems such as SPECT, PET, and MRI imaging systems. More particularly, the present invention detects faults in resistive position feedback sensors by detecting intermittent noise in an output signal of such sensors.

BACKGROUND OF THE INVENTION

Motion control systems typically utilize variable resistive devices, such as potentiometers or linear strip variable resistors, as low-cost, absolute position feedback sensors. Accurate motion control is critical in many system applications, especially in medical imaging systems such as SPECT, PET and MRI imaging systems where accurate positioning of movable components such as patient beds, gantries, detector heads, etc. is essential.

One disadvantage in the use of such variable resistive position sensors is that the electro-mechanical contact of such device can experience an intermittent or permanent failure. While a permanent failure is readily apparent, the susceptibility of specific resistive feedback sensors to intermittent failures can be difficult to identify when equipment is serviced because the failure may not occur during a service inspection. For example, where a contact is prone to intermittent failure due to a contaminant such as dirt or debris, or gradual deterioration of the contact material, movement of the variable resistive device could affect a temporary cleaning of the electro-mechanical contact and thus preclude detection of the underlying problem during servicing of the system. Accordingly, it would be desirable to have the capability of detecting intermittent failures of resistive feedback devices.

BRIEF SUMMARY OF THE INVENTION

The present invention solves the existing need in the art by providing mechanisms for detecting faults in resistive position feedback sensors that are common in the use of motion control systems. These mechanisms can be embodied in components separate from the motion control system, or incorporated into the programming of digital signal processors controlling the motion system.

According to a first embodiment, a filter mechanism is used to detect noise in an electro-mechanical contact of the variable resistive device. A filter receives an output signal of the resistive device, which is typically coupled to a motion control system through a feedback loop. The filter removes normal system noise from the signal. A memory stores occurrences of a noise signal passing the filter, which is indicative of an intermittent fault in the electromechanical contact of the position sensor. An alarm is activated in response to the noise signal, alerting a user that a failure is detected. A reset device can clear the memory when the fault has been repaired.

In a second embodiment, the mechanism of the first embodiment can be augmented to provide greater discrimination of noise indicative of intermittent failure. A motion control system includes a controller, a motor, a velocity sensor, and a resistive device. The output of the resistive device is coupled to the controller in a feedback loop, wherein the resistive device produces a feedback signal. The output of the velocity sensor is also coupled to the controller in a feedback loop. The velocity sensor output signal is inputted into an integrator, which develops a position signal. A subtractor circuit receives the resistive feedback signal and the position signal and produces a difference signal by subtracting the resistive feedback signal from the position signal. The difference signal passes through a filter and is further processed for the detection of noise. The memory stores intermittent occurrences of signals that pass through the filter. An alarm is activated by the noise signal, alerting a user that a failure is detected. A reset device can clear the memory when the failure has been repaired.

In a third embodiment, a fault detection circuit includes upper- and lower-limit comparators. The output signal of the variable resistive position sensor is connected to one of the inputs of each comparator. The second inputs of each comparator are set to either a low limit or a high limit. An error signal is generated by the comparators when the low or high limits are exceeded. A memory receives the error signal, and activates an alarm. A reset device can clear the memory when the sensor fault has been repaired.

Each component of the embodiments described above may also be used separately or in conjunction to detect failure of the variable resistive feedback device, which is independent of the motion control system.

BRIEF DESCRIPTION OF THE DRAWINGS

The invention now will be described in greater detail in the following by way of example only and with reference to the attached drawings, in which.

DETAILED DESCRIPTION OF THE INVENTION

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
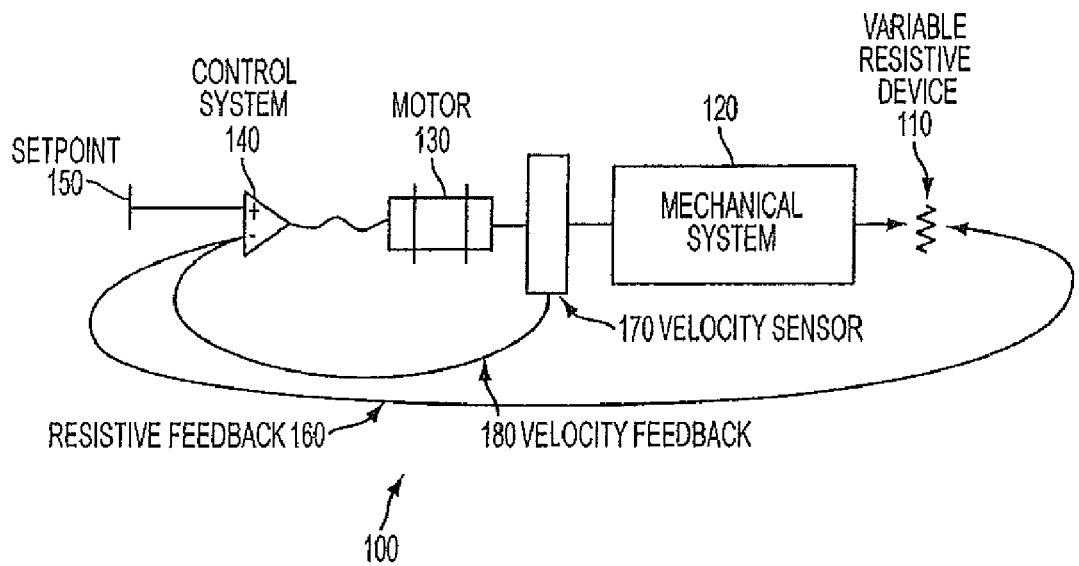
FIG. 1 is a diagram of a conventional motion control system with a resistive feedback position sensor, which is applicable to the present invention.

FIG. 1 depicts a typical motion control system with a resistive feedback sensor 100, which is applicable to the present invention. A variable resistive device 110 (such as a potentiometer, linear strip variable resistor, etc.) measures the absolute position of a mechanical system 120. The mechanical system 120 (which may be a gantry, patient bed, detector head, collimator tray, etc. of a nuclear imaging system such as a SPECT system, PET system, or a MRI system) is driven by a motor 130 which receives a signal from a motion control system 140. The output motor drive signal of the motion control system 140 is determined by the difference between a reference set point 150 and a resistive feedback signal 160 derived from the variable resistive device 110. In the simplest form, the control system 140 drives the motor 130 until the set-point 150 is equal to the feedback signal 160. In this system 100 the variable resistive device 110 can provide position and velocity information of mechanical system 120 for the control system 140. The variable resistive device 110 used in this embodiment can be implemented by, but is not limited to: a potentiometer, a digital controlled potentiometer, a variable resistor, and a linear strip variable resistor. Also, the control system 140 can be embodied as an analog controller, digital controller, or software-based controller.

An optional system could also include a velocity sensor 170 and a velocity feedback signal 180 part of the motion control system. In this alternative system the control system 140 drives the motor 130 until the set-point 150 is equal to a value derived from a combination of the resistive feedback signal 160 and the velocity feedback signal 180.

Figure 2:
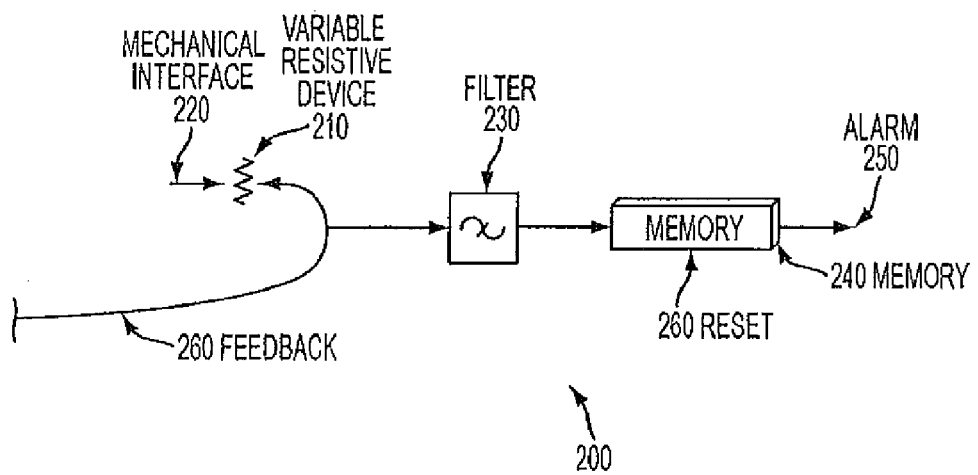
FIG. 2 is a diagram of an intermittent fault detection circuit for a variable resistive position sensor according to a first embodiment of the present invention.

FIG. 2 depicts an embodiment of a circuit 200 for detecting noise in an electro-mechanical contact of a variable resistive position sensor device in accordance with a first embodiment of the present invention. A variable resistive device 210 produces an output feedback position signal 260 in response to motion of a mechanical interface 220 (which may be any of the movable components of a medical imaging system as mentioned above, for example). The circuit 200 receives the resistive feedback signal 260 from variable resistive device 210, where it is fed to filter 230, which processes the incoming resistive feedback signal 260. The filter 230 is either a high-pass filter or band-pass filter that has a lower cutoff frequency above the normal frequency response of the system 100 components, which are listed as follows: mechanical system 120, motor 130, control system 140, and set-point 150. Electrical energy that passes through the filter 230 thus will correspond to noise produced by the electro-mechanical contact of the resistive device 210. Intermittent occurrences of signals passing through the filter 230 will be recorded and stored in a non-volatile memory 240, such as a solid state memory device, flash memory device, etc. The record of the event will remain in the memory 240 until a reset signal 260 produced by a user or by an external event (such as completion of repairs to the system) is applied to the memory to reset its contents. Upon receiving a signal from the filter 230, the memory 240 triggers an alarm 250, which indicates that a failure was detected. The alarm may be an audible alarm, visible alarm, or textual alarm, and also may be coupled if desired to other system control components to initiate appropriate action in response to a fault. The alarm alerts an operator that the system requires servicing. The system can be reset 260 after the repairs are completed.

Figure 3:
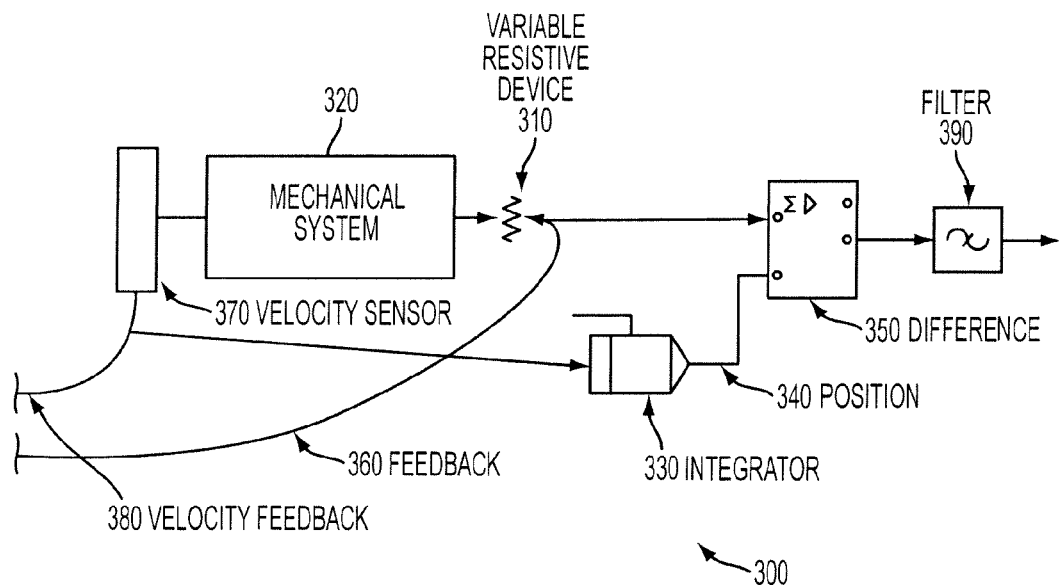
FIG. 3 is a diagram of an intermittent fault detection circuit for a variable resistive position sensor according to a second embodiment of the present invention.

FIG. 3 depicts a second embodiment 300 for detecting intermittent failures in variable resistive position sensors, which incorporates a velocity sensor 370 in the fault detection. The embodiment of FIG. 3 augments the embodiment 200 of FIG. 2 to provide greater discrimination of noise detection by incorporating a velocity feedback signal 380 from velocity sensor 370. The embodiment of FIG. 3 can be used, for example, when intermittent noise from the variable resistive position sensor falls into the same frequency band of "normal" system noise produced by the control system.

As shown in FIG. 3, an integrator 330 receives the velocity feedback signal 380 as an input. The integrator 330 integrates the velocity feedback signal 380 to develop a relative position signal 340, which is sent to a difference circuit 350. Difference circuit 350 receives the relative position signal 340 at one of it inputs, and receives the resistive feedback position signal 360 from variable resistive sensor device 310 at another of its inputs. The difference circuit 350 processes the variable resistive feedback position signal 360 and relative position signal 340 by calculating the difference between the two signals. A difference between the resistive feedback signal 360 and relative position signal 340 will produce a difference output signal. This difference output signal represents a difference between the response of the mechanical system 320 to driving by motor 130, and the response of the resistive device 310 to motion by the mechanical system 320. The typical noise bandwidth of the mechanical system 320 is much lower than the noise of a failed resistive device 310.

A filter 390 receives the difference output signal and filters it. The filter 390 is either a high-pass filter or band-pass filter that has a lower cutoff frequency above the frequency response of the system 300 components. Electrical energy that passes through the filter 390 will represent intermittent noise of the variable resistive device 310. Intermittent occurrences of signals passing through the filter 390 will be recorded and stored in a non-volatile memory (not shown; see memory 240, FIG. 2). The record of this event will remain in the memory until a reset signal is provided by an external event or by a user. The memory triggers an alarm which indicates that a failure was detected. The system can be reset after the repairs of the fault are completed.

Figure 4:
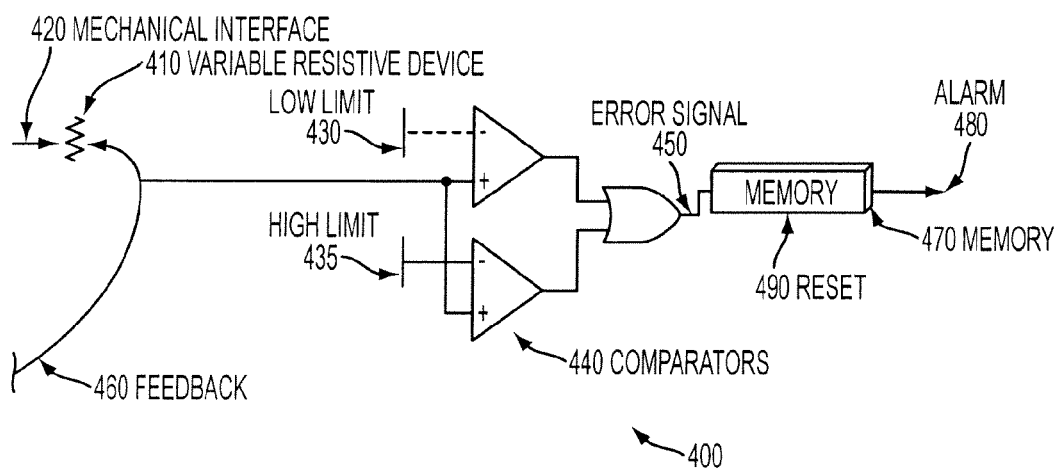
FIG. 4 is a diagram of an intermittent fault detection circuit for a variable resistive position sensor according to a third embodiment of the present invention.

FIG. 4 depicts a third embodiment 400 of the invention, in the form of a circuit for detecting intermittent faults in a variable resistive position sensor. The circuit 400 includes a variable resistive device 410 that produces a resistive feedback position signal 460. The resistive feedback position signal 460 is coupled to a first input terminal of each of a pair of comparators 440. A first comparator of the pair has a lower limit threshold value 430 applied to its second input terminal, while the second comparator of the pair has a high limit threshold value 435 applied to its second input terminal. The values of the high and low limits are predetermined by adding or subtracting values for the acceptable operating range of the control system during an evaluation period. At the end of the evaluation period the limits are recalculated and reassigned. The recalculation and reassignment of limits creates a dynamic range of acceptable values expected from the system. When the limit of either comparator 440 is exceeded an error signal 450 is produced.

The error signal 450 thus indicates a fault in the variable resistive device 410. As in FIG. 3, the velocity signal may be added to the determination of fault where the "normal" noise from other components of the motion control system are in the same frequency band as intermittent noise from the variable resistive position device. A memory 470 further processes the error signal 450 by recording the event. The recorded event that caused the error signal 450 remains in the memory 470 until a reset 490 signal is applied to reset the memory. The memory 470 triggers an alarm 480 which indicates that a failure was detected. This information can be used to alert an operator that the system requires servicing, or in leading an operator to an unnoticeable fault. The system can be reset after the repairs are completed.

Those skilled in the art will appreciate that embodiments of this invention may be practiced in any motion control environments including manufacturing control systems, electro-mechanical systems, power systems, etc.

The invention having been thus described, it will be apparent to those skilled in the art that the same may be varied in many ways without departing from the spirit and scope of the invention. Any and all such modifications are intended to be covered within the scope of the following claims.

What is claimed is:

1. A circuit for detecting intermittent faults in a variable resistive position sensing device, comprising:

a filter circuit for receiving a position signal of said variable resistive position sensing device and filtering said position signal to provide an output signal indicative of a fault in said variable resistive position sensing device;

a storage device for storing output signals from said filters indicative of faults in said variable resistive position sensing device;

wherein said filter circuit comprises a velocity sensor for providing a velocity signal;

an integrator that receives said velocity signal from said velocity sensor and integrates said velocity signal to produce a velocity sensor position signal, and a difference circuit that obtains a difference between said velocity sensor position signal and said variable resistive position signal, and outputs said difference as a difference signal, wherein said difference signal is applied to a high-pass or band-pass filter to produce said output signal.

2. The circuit of claim 1, wherein the filter circuit comprises a high-pass filter with a cutoff frequency above a frequency response of a motion control system of which said variable resistive position sensing device is a part.

3. The circuit of claim 1, wherein the filter circuit comprises a band-pass filter with a lower cutoff frequency above a frequency response of a motion control system of which said variable resistive position sensing device is a part.

4. The circuit of claim 1, wherein said storage device is a solid state memory device.

5. The circuit of claim 1, further comprising an alarm that is activated upon occurrence of an output signal from said filter circuit.

6. The circuit of claim 5, wherein said alarm is activated by a signal from said storage device.

7. The circuit of claim 1, further comprising a reset signal applied to said storage device by an external event, which reset signal resets said storage device to an initial state.

8. The circuit of claim 1, wherein said filter circuit comprises a pair of comparators, respectively comparing said position signal with predetermined low and high limit values, such that an output signal is produced when said position signal is higher than said high limit value or lower than said low limit value.

9. A motion control system, comprising:
a motion controller;
a motor;
a variable resistive position sensor;
a feedback loop coupled to an output of said variable resistive position sensor and providing a variable resistive position feedback signal to said motion controller;
a filter circuit also coupled to said output of said variable resistive position sensor and filtering said variable resistive position feedback signal to produce a fault signal indicative of a fault in said variable resistive position sensor;
a storage device for storing a fault signal from said filter circuit;
wherein said filter circuit comprises a velocity sensor for providing a velocity signal;
an integrator that receives said velocity signal from said velocity sensor and integrates said velocity signal to produce a velocity sensor position signal, and
a difference circuit that obtains a difference between said velocity sensor position signal and said variable resistive position signal, and outputs said difference as a difference signal, wherein said difference signal is applied to a high-pass or band-pass filter to produce an output signal.

10. The motion control system of claim 9, wherein the filter circuit comprises a high-pass filter with a cutoff frequency above a frequency response of said motion control system.

11. The motion control system of claim 9, wherein the filter circuit comprises a band-pass filter with a lower cutoff frequency above a frequency response of said motion control system.

12. The motion control system of claim 9, wherein said storage device is a solid state memory device.

13. The motion control system of claim 9, further comprising an alarm that is activated upon occurrence of an output signal from said filter circuit.

14. The motion control system of claim 13, wherein said alarm is activated by a signal from said storage device.

15. The motion control system of claim 9, further comprising a reset signal applied to said storage device by an external event, which reset signal resets said storage device to an initial state.

16. The motion control system of claim 9, wherein said filter circuit comprises a pair of comparators, respectively comparing said position signal with predetermined low and high limit values, such that an output signal is produced when said position signal is higher than said high limit value or lower than said low limit value.

17. A medical imaging system, comprising:
a movable mechanical component;
a motion controller that controls motion of said movable mechanical component;
a motor that moves said movable mechanical component in response to a signal from said controller;
a variable resistive position sensor that determines a position of said movable mechanical component;
a feedback loop coupled to an output of said variable resistive position sensor and providing a variable resistive position feedback signal to said motion controller;
a filter circuit also coupled to said output of said variable resistive position sensor and filtering said variable resistive position feedback signal to produce a fault signal indicative of a fault in said variable resistive position sensor; and
a storage device for storing a fault signal from said filter circuit
wherein said filter circuit comprises a velocity sensor for providing a velocity signal;
an integrator that receives said velocity signal from said velocity sensor and integrates said velocity signal to produce a velocity sensor position signal, and
a difference circuit that obtains a difference between said velocity sensor position signal and said variable resistive position signal, and outputs said difference as a difference signal, wherein said difference signal is applied to a high-pass or band-pass filter to produce an output signal.

18. The medical imaging system of claim 17, wherein said movable mechanical component comprises a radiation detector.

* * * * *